United States Patent [19]

Junino et al.

[11] Patent Number: 5,710,311
[45] Date of Patent: Jan. 20, 1998

[54] 2-SULPHURED METAPHENYLENEDIAMINES FOR DYEING HAIR

[75] Inventors: Alex Junino, Livry-Gargan; Alain Genet, Aulnay-sous-Bois; Alain Lagrange, Coupvray, all of France

[73] Assignee: L'Oreal, France

[21] Appl. No.: 536,369

[22] Filed: Sep. 29, 1995

Related U.S. Application Data

[63] Continuation of Ser. No. 162,011, filed as PCT/FR93/00294 Mar. 24, 1993, Pat. No. 5,505,741.

[30] Foreign Application Priority Data

Mar. 25, 1992 [FR] France .................. 92 03614

[51] Int. Cl.$^6$ .............. C07C 255/34; C07C 321/06; C07C 323/29; C07C 381/06
[52] U.S. Cl. .............. 558/414; 558/418; 560/18; 562/432; 564/154; 564/162
[58] Field of Search .................. 564/305, 306, 564/440, 154, 162; 562/432; 560/18; 558/414, 418

[56] References Cited

U.S. PATENT DOCUMENTS

| | | | |
|---|---|---|---|
| 1,940,757 | 6/1933 | Lehmann et al. | 8/5 |
| 4,085,217 | 4/1978 | Kalopissi | 424/266 |
| 4,146,688 | 3/1979 | Schwindt et al. | 521/159 |
| 4,260,634 | 4/1981 | Wehrmeister | 424/324 |
| 4,973,760 | 11/1990 | Davis | 564/440 |

FOREIGN PATENT DOCUMENTS 3343642  6/1985  Germany .

OTHER PUBLICATIONS

Patent Abstracts of Japan, vol. 004, No. 073 (C.012) May 1980 (Abstract of 55-38334—Mar. 1980).
English Language Translation of DE 3,343,642, Henkel KGaA, Jun. 1985.

*Primary Examiner*—Johann Richter
*Assistant Examiner*—Ebenezer Sackey
*Attorney, Agent, or Firm*—Cushman Darby & Cushman IP Group of Pillsbury Madison & Sutro LLP

[57] ABSTRACT

At least one 2-sulphured metaphenylenediamine of formula (I)

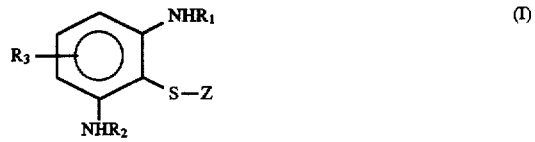

used for dyeing keratin fibres, wherein Z is alkyl, aralkyl, monohydroxyalkyl, polyhydroxyalkyl, aryl or aminoalkyl; $R_1$ and $R_2$, which are the same or different, are hydrogen, alkyl, monohydroxyalkyl, polyhydroxyalkyl, monocarbamylalkyl, dialkylcarbamyl, aminoalkyl, acyl carbalkoxy, carbamyl, or monoalkylcarbamyl; $R_3$ is hydrogen, alkyl, nitrile, amide, fluoroalkyl, or —COOR; and the corresponding acid salts. A method for dyeing keratin fibres, and novel 2-sulphured metaphenylenediamines, are also disclosed.

2 Claims, No Drawings

2-SULPHURED METAPHENYLENEDIAMINES FOR DYEING HAIR

This is a continuation of application Ser. No. 08/162,011, filed Nov. 23, 1993 now U.S. Pat. No. 5,505,741 which is a 371 of PCT/FR93/00294 Mar. 24, 1993.

The present invention relates to the use for dyeing keratinous fibers and more particularly human hair of 2-sulfurated metaphenylenediamines, to dyeing compositions containing these 2-sulfurated metaphenylenediamines, to a dyeing process using these compositions and to novel sulfurated metaphenylenediamines and their process of preparation.

Sulfurated derivatives of aromatic amines, in combination with oxidation dye precursors, have already been used for dyeing keratinous fibers.

It is known to dye keratinous fibers and in particular human hair with dyeing compositions containing oxidation dye precursors and couplers.

The couplers, also called the coloring modifiers, make it possible to vary the shades obtained with the oxidation dye precursors.

In the field of dyeing keratinous fibers and in particular human hair, the search is for couplers which, in combination with oxidation dye precursors, make it possible to obtain a wide range of shades, while conferring on hair a coloring having a satisfactory resistance to light, to washing, to bad weather, to perspiration and to the various treatments which hair may be subjected to.

The applicants have discovered, which forms the subject of the invention, that the use of certain 2-sulfurated metaphenylenediamines as couplers with oxidation dye precursors of ortho and/or para type in dyeing compositions for keratinous fibers made it possible to obtain, on application to keratinous fibers and in particular human hair, a wide range of coloring shades exhibiting a particularly outstanding resistance to light, to washing, to bad weather, to perspiration and to the various treatments which hair may be subjected to.

The invention applies to the use of these 2-sulfurated metaphenylenediamines for dyeing keratinous fibers and in particular human hair.

Another subject of the invention consists of oxidation dyeing compositions, intended to be used for dyeing keratinous fibers and in particular human hair, containing at least one oxidation dye precursor of ortho and/or para type and at least certain 2-sulfurated metaphenylenediamines.

The invention also applies to the process for coloring keratinous fibers and in particular human hair using such a composition mixed with an oxidizing agent.

Another subject of the invention is novel 2-sulfurated metaphenylenediamines and their process of preparation.

Other subjects of the invention will become apparent on reading the description and examples which follow.

The subject of the present invention is thus the use, for dyeing keratinous fibers and in particular human hair, of at least one 2-sulfurated metaphenylenediamine of general formula:

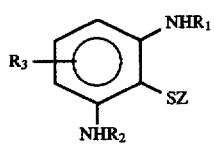

in which: Z represents a $C_1$–$C_{18}$ alkyl radical, an aralkyl radical in which the alkyl radical is $C_1$–$C_6$, a $C_1$–$C_6$ mono-hydroxyalkyl or $C_2$–$C_6$ polyhydroxyalkyl radical, an aryl radical or an aminoalkyl radical of formula:

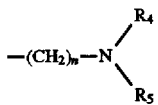

in which n is an integer between 1 and 6 inclusive and $R_4$ and $R_5$, which are identical or different, represent a hydrogen atom or a $C_1$–$C_4$ alkyl, $C_1$–$C_4$ hydroxyalkyl or $C_1$–$C_6$ acyl radical;

$R_1$ and $R_2$, which are identical or different, represent a hydrogen atom, a $C_1$–$C_6$ alkyl radical, a $C_1$–$C_6$ monohydroxyalkyl radical, a $C_2$–$C_6$ polyhydroxyalkyl radical, a $C_1$–$C_6$ monocarbamoylalkyl radical, a $C_1$–$C_6$ dialkylcarbamoyl radical, a $C_1$–$C_6$ aminoalkyl radical, a $C_1$–$C_6$ acyl radical, a $C_2$–$C_6$ carbalkoxy radical, a carbamoyl radical or a $C_1$–$C_6$ monoalkylcarbamoyl radical;

$R_3$ represents a hydrogen atom, a $C_1$–$C_4$ alkyl radical, a nitrile radical, an amide radical, a $C_1$–$C_4$ fluoroalkyl radical or a radical —COOR where R represents a hydrogen atom or a $C_1$–$C_4$ alkyl radical, and the acid salts corresponding to the compounds of formula (I).

Among the preferred meanings of the Z radical in the sulfurated metaphenylenediamines of general formula (I) according to the invention, the $C_1$–$C_{18}$ alkyl radical denotes the methyl, ethyl, propyl, butyl, dodecyl or hexadecyl radicals; the aralkyl radical denotes the benzyl radical; the mono- or polyhydroxyalkyl radical denotes —CH$_2$—CH$_2$OH, —CH$_2$—CHOH—CH$_2$—OH or —CH$_2$—CHOH—CH$_3$; the aryl radical denotes phenyl; the aminoalkyl radical denotes

—CH$_2$—CH$_2$—NH$_2$, —CH$_2$—CH$_2$—NHCH$_3$, $$-CH_2-CH_2-\underset{\underset{CH_3}{|}}{N}-COCH_3$$

and

—CH$_2$—CH$_2$—NHCOCH$_3$;

when the $R_1$, $R_2$, $R_4$ and $R_5$ groups represent an acyl radical, the latter preferably denotes the formyl, acetyl and propionyl radicals.

When the $R_3$ group denotes an alkyl radical, the latter is a methyl, ethyl, n-propyl, isopropyl, n-butyl or isobutyl radical.

Among the fluoroalkyl radicals, mention may be made of trifluoromethyl and trifluoroethyl.

The acid salts corresponding to the sulfurated metaphenylenediamine compounds of general formula (I) are preferably chosen from the hydrochlorides, sulfates or hydrobromides.

Mention may be made, among the sulfurated metaphenylenediamines of general formula (I), of:

2-β-acetylaminoethylthio-1,3-diaminobenzene,
2-methylthio-5-methyl-1,3-diaminobenzene,
2-methylthio-5-amido-1,3-diaminobenzene,
2-methylthio-5-nitrilo-1,3-diaminobenzene,
2-methylthio-5-trifluoromethyl-1,3-diaminobenzene,
2-methylthio-1,3-diaminobenzene,
2-methylthio-3-amino-1-(carbamoyl-t-butyl)benzene,
2-methylthio-1,3-di(carbamoyl-t-butyl)benzene,
2-methylthio-1,3-diacetylaminobenzene,
2-n-propylthio-5-trifluoromethyl-1,3-diaminobenzene, 2-isopropylthio-5-trifluoromethyl-1,3-diaminobenzene,
2-methylthio-4-methyl-1,3-diaminobenzene,
2-ethylthio-5-trifluoromethyl-1,3-diaminobenzene,
2-isobutylthio-5-trifluoromethyl-1,3-diaminobenzene,
2-n-butylthio-5-trifluoromethyl-1,3-diaminobenzene,
and their acid salts.

The more particularly preferred compounds are:
2-β-acetylaminoethylthio-1,3-diaminobenzene,
2-methylthio-5-methyl-1,3-diaminobenzene,
2-methylthio-5-amido-1,3-diaminobenzene,
2-methylthio-5-nitrilo-1,3-diaminobenzene,
2-methylthio-5-trifluoromethyl-1,3-diaminobenzene,
2-methylthio-1,3-diaminobenzene
and their acid salts.

The compounds of formula (I) can be used as couplers in the presence of oxidation dye precursors of ortho and/or para type known in themselves making it possible to dye hair by oxidation coloring according to a process using an oxidative condensation reaction of the precursors and of the coupler.

The dye precursors of ortho and/or para type are compounds which are not dyes in themselves but which form a dye by an oxidative condensation process either with themselves or in the presence of a coupler or modifier.

These oxidation dye precursors of ortho or para type are benzene or heterocyclic compounds which contain two functional groups, amino or hydroxyl and amino, in positions ortho or para with respect to one another.

Oxidation dye precursors of ortho or para type can be chosen from paraphenylenediamines, paraaminophenols, para heterocyclic precursors derived from pyridine or pyrimidine, such as 2,5-diaminopyridine, 2-hydroxy-5-aminopyridine, 2,4,5,6-tetraaminopyrimidine, 4,5-diamino-1-methylpyrazole or 2-dimethylamino-4,5,6-triaminopyrimidine, orthoaminophenols and the so-called "double" bases.

As paraphenylenediamines, there may more particularly be mentioned the compounds corresponding to the formula (III):

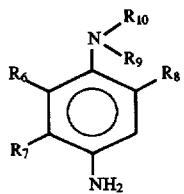

in which:
- $R_6$, $R_7$ and $R_8$, which are identical or different, represent a hydrogen or halogen atom, an alkyl radical, an alkoxy radical or a $C_1$-$C_4$ hydroxyalkyl, sulfo or carboxyl radical;
- $R_9$ and $R_{10}$, which are identical or different, represent a hydrogen atom or an alkyl, hydroxyalkyl, alkoxyalkyl, carbamoylalkyl, mesylaminoalkyl, acetylaminoalkyl, ureidoalkyl, carbalkoxyaminoalkyl, sulfoalkyl, piperidinoalkyl, morpholinoalkyl or phenyl radical, the phenyl radical optionally being substituted in the para position by an amino group; or else $R_9$ and $R_{10}$ form, jointly with the nitrogen atom to which they are bonded, a piperidino or morpholino heterocycle, with the proviso that $R_6$ or $R_8$ represents a hydrogen atom when $R_9$ and $R_{10}$ do not represent a hydrogen atom, and the salts of these compounds. These alkyl or alkoxy radicals preferably have 1 to 4 carbon atoms end denote especially methyl, ethyl, propyl, methoxy and ethoxy radicals.

Among compounds of formula (III), mention may more particularly be made of paraphenylenediamine, p-toluylenediamine, methoxyparaphenylenediamine, chloroparaphenylenediamine, 2,3-dimethylparaphenylenediamine, 2,6-dimethylparaphenylenediamine, 2,6-diethylparaphenylenediamine, 2,5-dimethylparaphenylenediamine, 2-methyl-5-methoxyparaphenylenediamine, 2,6-dimethyl-5-methoxyparaphenylenediamine, N,N-dimethylparaphenylenediamine, N,N-diethylparaphenylenediamine, N,N-dipropylparaphenylenediamine, 3-methyl-4-amino-N,N-diethylaniline, N,N-di(β-hydroxyethyl) paraphenylenediamine, 3-methyl-4-amino-N,N-di(β-hydroxyethyl)aniline, 3-chloro-4-amino-N,N-di(β-hydroxyethyl)aniline, 4-amino-N,N-(ethyl, carbamoylmethyl)aniline, 3-methyl-4-amino-N,N-(ethyl, carbamoylmethyl)aniline, 4-amino-N,N-(ethyl, (β-piperidinoethyl)aniline, 3-methyl-4-amino-N,N-(ethyl,β-piperidinoethyl)aniline, 4-amino-N,N-(ethyl,β-morpholinoethyl)aniline, 3-methyl-4-amino-N,N-(ethyl,β-morpholinoethyl)aniline, 4-amino-N,N-(ethyl,β-acetylaminoethyl)aniline, 4-amino-N-(β-methoxyethyl) aniline, 3-methyl-4-amino-N,N-(ethyl, β-acetylaminoethyl) aniline, 4-amino-N,N-(ethyl,β-mesylaminoethyl)aniline, 3-methyl-4-amino-N,N-(ethyl, β-mesylaminoethyl) aniline, 4-amino-N,N-(ethyl, β-sulfoethyl)aniline, 3-methyl-4-amino-N,N-(ethyl, β-sulfoethyl)aniline, N-[(4'-amino)phenyl]-morpholine, N-[(4'-amino)phenyl]piperidine, 2-hydroxyethylparaphenylenediamine, fluoroparaphenylenediamine, carboxyparaphenylenediamine, sulfoparaphenylenediamine, 2-isopropylparaphenylenediamine, 2-n-propylparahenylenediamine, hydroxy-2-(n-propyl) paraphenylenediamine, 2-hydroxymethylparaphenylenediamine, N,N-dimethyl-3-methylparaphenylenediamine, N,N-(ethyl, β-hydroxy-ethyl) paraphenylenediamine, N-(dihydroxypropyl) paraphenylenediamine, N-4'-aminophenylparaphenylenediamine or N-phenylparaphenylenediamine.

These paraphenylenediamines can be used either in the free base form or in the form of salts, such as hydrochloride, hydrobromide or sulfate.

Among the p-aminophenols, mention may be made of p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl) 4-aminophenol, 2-methoxy-4-aminophenol, 3-methoxy-4-aminophenol, 3-(β-hydroxyethoxy)4-aminophenol, 2-methoxymethyl-4-aminophenol, 2-aminomethyl-4-aminophenol, 2-(β-hydroxyethylaminomethyl)-4-aminophenol, 2-ethoxymethyl-4-aminophenol or 2-[(β-hydroxyethoxy)-methyl]-4-aminophenol.

The so-called "double" bases are bisphenylalkylenediamines, corresponding to the formula:

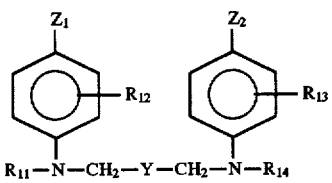

(IV)

in which:

Z₁ and Z₂, which are identical or different, represent hydroxyl groups or groups $NHR_{15}$ where $R_{15}$ denotes a hydrogen atom or a lower alkyl radical;

$R_{12}$ and $R_{13}$, which are identical or different, represent either hydrogen atoms, or halogen atoms, or also alkyl radicals;

$R_{11}$ and $R_{14}$, which are identical or different, represent a hydrogen atom or an alkyl, hydroxyalkyl or aminoalkyl radical, it being possible for the amino residue to be substituted;

Y represents a radical taken from the group consisting of the following radicals:

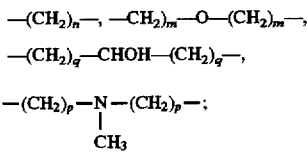

in which n is an integer between 0 and 8 and m, q and p are integers between 0 and 4, it also being possible for this base to be provided in the form of its addition salts with acids.

The alkyl or alkoxy radicals shown above preferably denote a group having 1 to 4 carbon atoms and especially methyl, ethyl, propyl, methoxy and ethoxy.

Among the compounds of formula (IV), there may be mentioned N,N'-bis(β-hydroethyl)N,N'-bis(4'-aminophenyl)-1,3-diamino-2-propanol, N,N'-bis(β-hydroxyethyl)N,N'-bis (4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine.

Among the ortho-aminophenols, mention may more particularly be made of 1-amino-2-hydroxybenzene, 6-methyl-1-hydroxy-2-aminobenzene, 4-methyl-1-amino-2-hydroxybenzene or 4-acetylamino-1-amino-2-hydroxybenzene.

The compounds of formula (I) are applied to keratinous fibers and in particular human hair by means of dyeing compositions which constitute another subject of the invention.

The compositions in accordance with the invention contain, in a suitable medium for dyeing, at least one 2-sulfurated metaphenylenediamine defined above. The preferred compositions contain at least one 2-sulfurated metaphenylenediamine defined above in combination with at least one oxidation dye precursor as defined above.

The dyeing compositions in accordance with the invention can also contain, in addition to the coupler corresponding to the formula (I) defined above, other couplers known in themselves, such as metadiphenols, metaaminophenols, metaphenylenediamines other than those of formula (I) above, metaacylaminophenols, metaureidophenols, metacarbalkoxyaminophenols, α-naphthol, indole derivatives or couplers having an active methylene group, such as β-keto compounds or pyrazolones.

Among these couplers, there may be more particularly mentioned 2,4-dihydroxyphenoxyethanol, 2,4-dihydroxyanisole, metaaminophenol, resorcinol monomethyl ether, resorcinol, 2-methylresorcinol, 2-methyl-5-aminophenol, 2-methyl-5-N-(β-hydroxyethyl)aminophenol, 2-methyl-5-N-(β-mesylaminoethyl)aminophenol, 2,6-dimethyl-3-aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]phenoxyethanol, 2-amino-4-N-(β-hydroxyethyl)aminoanisole, (2,4-diamino) phenyl-β-γ-dihydroxypropyl ether, 2,4-diaminophenoxyethylamine, 1,3-dimethoxy-2,4-diaminobenzene, 1,3,5-trimethoxy-2,4-diaminobenzene, 1-amino-3,4-methylenedioxybenzene, 1-hydroxy-3,4-methylenedioxybenzene, 2-chloro-6-methyl-3-aminophenol, 2-methyl-3-aminophenol, 2-chlororesorcinol, 6-methoxy-3-hydroxyethylaminoaniline, 1-ethoxy-2-bis(β-hydroxyethyl)amino-4-aminobenzene, 3-diethylaminophenol, 1,3-dihydroxy-2-methylbenzene, 1-hydroxy-2,4-dichloro-3-aminobenzene, 4,6-hydroxyethoxy-1,3-diaminobenzene, 4-methyl-6-ethoxy-1,3-diaminobenzene, 4-chloro-6-methyl-3-aminophenol, 6-chloro-3-trifluoroethylaminophenol and their salts.

There may be added to these compositions, as is well known in the state of the art, especially for the purpose of shading or enriching in highlights the colorings introduced by the oxidation dye precursors, direct dyes such as azo dyes, anthraquinone dyes or nitrated derivatives of the benzene series.

The combined oxidation dye precursors of para and/or ortho type, as well as the couplers used in the dyeing compositions in accordance with the invention, preferably represent from 0.3 to 7% by weight with respect to the weight of the said composition. The concentration of sulfurated metaphenylenediamine compounds of formula (I) can vary between 0.05 and 3.5% by weight of the total weight of the composition.

The dyeing compositions in accordance with the invention also contain, in their preferred embodiment, anionic, cationic, nonionic or amphoteric surface-active agents or their mixtures. Among these surface-active agents, there may be mentioned alkylbenzenesulfonates, alkylnaphthalenesulfonates, sulfates, ethersulfates and fatty alcohol sulfonates, quaternary ammonium salts such as trimethylcetylammonium bromide or cetylpyridinium bromide, optionally oxyethylenated fatty acid ethanolamides, polyglycerolated fatty alcohols, polyoxyethylenated or polyglycerolated alkylphenols, and polyoxyethylenated alkylsulfates.

These surface-active agents are present in the compositions in accordance with the invention in proportions between 0.5 and 55% by weight, and preferably between 2 and 50% by weight, with respect to the total weight of the composition.

These compositions can also contain organic solvents for solubilizing the components which would not be sufficiently soluble in water. Among these solvents, there may be mentioned, by way of example, $C_1$–$C_4$ lower alkanols, such as ethanol and isopropanol; glycerol; glycols or glycol ethers such as 2-butoxyethanol, ethylene glycol, propylene glycol or the monoethyl ether and the monomethyl ether of diethylene glycol, and aromatic alcohols such as benzyl alcohol or phenoxyethanol, the analogous products and their mixtures.

The solvents are preferably present in proportions of between 1 and 40% by weight, and in particular between 5 and 30% by weight, with respect to the total weight of the composition.

The thickening agent which it is possible to add to the compositions in accordance with the invention can be chosen from sodium alginate, gum arabic, optionally crosslinked acrylic acid polymers, cellulose derivatives, or heterobiopolysaccharides, such as xanthan gum. It is also possible to use inorganic thickening agents such as bentonite.

These thickening agents are preferably present in proportions of between 0.1 and 5%, and in particular between 0.2 and 3%, by weight with respect to the total weight of the composition.

The antioxidizing agents which can be present in the compositions are chosen in particular from sodium sulfite, thioglycolic acid, sodium bisulfite, dehydroascorbic acid, hydroquinone and homogentisic acid. These antioxidizing agents are present in the composition in proportions of between 0.05 and 1.5% by weight with respect to the total weight of the composition.

The pH of these compositions is between 4 and 11. It is adjusted to the desired value using basifying agents well known in the state of the art, such as aqueous ammonia, alkali metal carbonates, alkanolamines such as mono-, di- and triethanolamines and their derivatives or sodium and potassium hydroxides, or conventional acidifying agents, such as inorganic or organic acids, such as hydrochloric, tartaric, citric, phosporic and sulfonic acid.

These compositions can also contain other cosmetically acceptable adjuvants, such as, for example, penetration agents, sequestering agents, fragrances, buffers, and the like.

The compositions in accordance with the invention can be provided in various forms, such as in the liquid, cream or gel form or any other form suitable for carrying out dyeing of keratinous fibers and especially of human hair. These compositions can be packaged in aerosol containers in the presence of a propellant and can form foams.

The compounds of formula (I) are used in accordance with the invention according to a process comprising the application to keratinous fibers of the compound of formula (I) and of ortho and/or para oxidation dye precursors in the presence of an oxidizing agent.

The dyeing compositions in accordance with the invention containing an oxidation dye precursor of the para and/or ortho type and a coupler of formula (I) are used according to a process in which development is implemented by an oxidizing agent.

In accordance with this process, the dyeing composition described above is mixed, at the time of use, with an oxidizing solution in an amount sufficient to be able to develop a coloring and the mixture obtained is then applied to keratinous fibers and in particular human hair.

The pH of the composition applied to hair preferably varies between 3 and 11. It is adjusted to the desired value using basifying agents well known in the state of the art, such as aqueous ammonia, alkali metal carbonates, alkanolamines such as mono-, di- and triethanolamine and their derivatives, or sodium or potassium hydroxide, or standard acidifying agents, such as inorganic or organic acids, such as hydrochloric, tartaric, citric, phosphoric and sulfonic acids. The oxidizing solution contains, as oxidizing agent, hydrogen peroxide, urea hydrogen peroxide, persalts, such as ammonium persulfate, organic peracids and their salts or alkali metal bromates. A 20 volumes hydrogen peroxide solution is preferably used.

The mixture obtained is applied to hair and is exposed for 10 to 40 minutes, preferably 15 to 30 minutes, after which it is rinsed, washed with shampoo, rinsed again and dried.

The coupler of formula (I) defined above can also be used in a multi-stage process, consisting, in one of the stages, in applying the oxidation dye precursor of ortho and/or para type or their mixture and, in another stage, in applying a dyeing composition containing the coupler of formula (I).

The oxidizing agent can be introduced, just before application, into the composition applied in the second stage or else be applied to the keratinous fibers themselves, in a third stage, the exposure, pH, washing and drying conditions being identical to those indicated above.

Another subject of the invention consists of novel 2-sulfurated metaphenylenediamines which correspond to the formula:

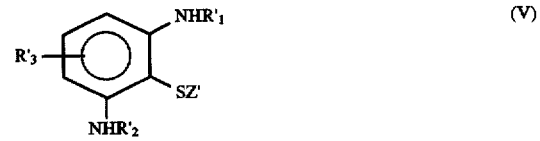

in which: Z' represents a $C_1$–$C_{18}$ alkyl radical, an aralkyl radical in which the alkyl radical is $C_1$–$C_6$, a $C_1$–$C_6$ monohydroxyalkyl or $C_2$–$C_6$ polyhydroxyalkyl radical, an aryl radical, an aminoalkyl radical of formula:

in which n is an integer between 1 and 6 inclusive; $R'_4$ and $R'_5$, which are identical or different, represent a hydrogen atom or a $C_1$–$C_4$ alkyl, $C_1$–$C_4$ hydroxyalkyl or $C_1$–$C_6$ acyl radical; $R'_1$ and $R'_2$, which are identical or different, represent a hydrogen atom, a $C_1$–$C_6$ alkyl radical, a $C_1$–$C_6$ monohydroxyalkyl radical, a $C_2$–$C_6$ polyhydroxyalkyl radical, a $C_1$–$C_6$ monocarbamoylalkyl radical, a $C_1$–$C_6$ dialkylcarbamoyl radical, a $C_1$–$C_6$ aminoalkyl radical, a $C_1$–$C_6$ acyl radical, a $C_2$–$C_6$ carbalkoxy radical, a carbamoyl radical or a $C_1$–$C_6$ monoalkylcarbamoyl radical;

$R_3$ represents a hydrogen atom or a $C_1$–$C_4$ alkyl, nitrile, amide, $C_1$–$C_4$ fluoroalkyl or —COOR radical where R represents a hydrogen atom or a $C_1$–$C_4$ alkyl radical; and their acid salts, with the proviso that:

when $R'_1$, $R'_2$ and $R'_3$ represent a hydrogen atom, Z' is other than the alkyl radical or the aryl radical;

when Z' represents the methyl radical and $R'_3$ represents hydrogen, $R'_1$ and $R'_2$ cannot both represent the same $C_1$–$C_6$ acyl radical;

when Z' represents the methyl radical and $R'_3$ represents hydrogen and when one of the two $R'_1$ and $R'_2$ radicals represents a hydrogen atom, the other $R'_1$ or $R'_2$ radical cannot represent a $C_4$ acyl radical;

when $R'_1$ and $R'_2$ represent hydrogen and $R'_3$ represents a trifluoromethyl radical in the 5 position, Z cannot represent a $C_1$–$C_4$ alkyl radical;

when $R'_1$ and $R'_2$ represent hydrogen and $R'_3$ represents a methyl radical in the 4 position, Z' cannot denote methyl.

Among compounds corresponding to formula (V) defined above, mention may preferably be made of 2-(β-acetylaminoethylthio)-1,3-diaminobenzene, 2-methylthio-5-methyl-1,3-diaminobenzene, 2-methylthio-5-amido-1,3-diaminobenzene and 2-methylthio-5-nitrilo-1,3-diaminobenzene.

Another subject of the invention is the dyeing compositions of the type defined above containing the compounds of formula (V) and the use of these compounds for dyeing keratinous fibers.

The sulfurated metaphenylenediamines of formula (V) or their salts can be prepared according to a multi-stage process.

According to a first process and in a first stage, halo-2, 6-dinitrobenzene or a substituted derivative is reacted, in the presence of a base such as potassium hydroxide or potassium carbonate, with a thiol of formula (VI):

in which $Z_1$ represents a $C_1$–$C_{18}$ alkyl radical, an aralkyl radical in which the alkyl radical is $C_1$–$C_6$, $C_1$–$C_6$ monohydroxyalkyl radical, a $C_2$–$C_6$ polyhydroxyalkyl radical, an aryl radical or a group of formula (VII):

in which $R'_4$ and n have the meanings shown above in the formula (V); and $R_{16}$ represents a hydrogen atom or a $C_1$–$C_3$ alkyl radical;

in a second stage, the nitro substituents of the compound of formula (VIII):

obtained previously are reduced to prepare a compound corresponding to the formula (IX):

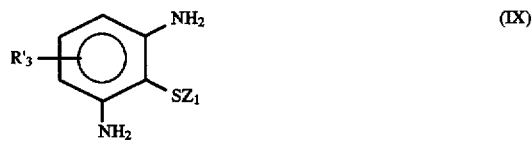

in which $Z_1$ has the meaning shown above;

optionally, in a third stage, and depending on the sulfurated metaphenylenediamine of formula (I) which it is desired to obtain, there is carried out a) either a monosubstitution of the aromatic amines to obtain a compound of formula (I) in which $R'_1$ and/or $R'_2$ are other than H, b) or an acid hydrolysis of the compound of formula (IX) in which $Z_1$ represents the group of formula (VII) to obtain the compound of formula (X)

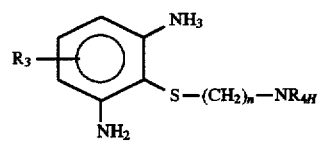

in which $R'_4$ and n have the meanings shown above, $R'_4$ not, however, denoting $C_1$–$C_6$ acyl radical, it being possible for the amines attached to the nucleus, to then be monosubstituted.

c) or, beforehand, the amine in the compound of formula (IX) which is not attached to the nucleus is substituted to obtain the compound of formula (XI)

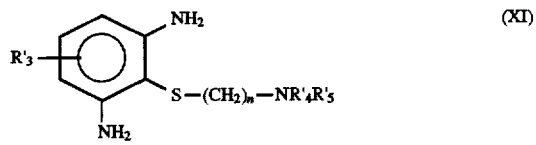

in which $R'_4$, $R'_5$ and n have the meanings shown above, it being possible for the amines which are attached to the nucleus to then be monosubstituted.

According to a second process and in a first stage, a substituted fluoronitrobenzene of formula (XII)

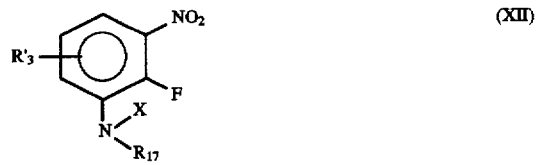

in which $R_{17}$ represents a $C_1$–$C_6$ acyl group and X represents hydrogen, or else $R_{17}$ and X form, jointly with the nitrogen atom to which they are bonded, an oxazolidone ring, is reacted with a thiol of formula:

in which M is an alkali metal and $Z_1$ has the meanings shown above.

In a second stage, the nitro substituent of the compound of formula (XIV)

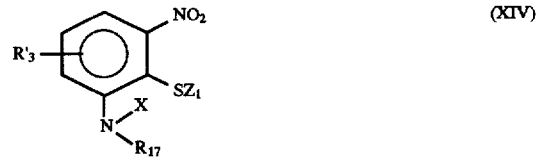

obtained above is reduced to obtain the compound of formula (XV)

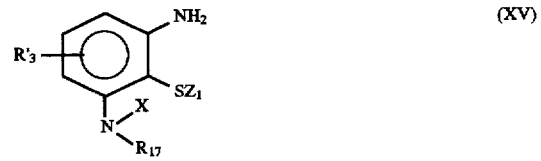

in which $R_{17}$ and X have the meanings shown above; optionally, in a third stage, and depending on the 2-sulfurated metaphenylenediamine of formula (I) which it is desired to obtain, the aromatic amine is monosubstituted to obtain a compound of formula (I) in which $R'_1$ or $R'_2$ is other than H.

Finally, in a last stage, the compound is subjected to acid hydrolysis in order to cleave the protective group.

The reduction of the nitro groups is preferably carried out by using iron in acetic medium or else with cyclohexene in the presence of a palladium/charcoal catalyst or by any other standard reduction process.

The substitution of the aromatic amines or of the amine which is not attached to the nucleus can be carried out by reacting with, for example, ethyl bromide, glycol bromohydrin, ethyl-chloroformate, β-chloroacetamide or acetic anhydride.

The examples which follow are intended to illustrate the invention without, however, any limiting nature being implied.

PREPARATION EXAMPLES

Example 1

Preparation of 2-methylthio-1,3-diaminobenzene dihydrochloride

A solution of 24.3 g (0.12 mol) of 2-chloro-1,3-dinitrobenzene in 60 ml of dimethoxyethane is added dropwise, over ½ hour and while maintaining the temperature between 20° and 25° C., to a suspension of 16.8 g (0.24 mol) of sodium thiomethylate in 120 ml of dimethoxyethane. After stirring for 30 minutes at room temperature, the reaction medium (brown suspension) is run into 800 ml of ice-cold water.

The oily precipitate is extracted with ethyl acetate. After treating with Ceca charcoal and with dry sodium sulfate, the ethyl acetate phase is filtered through paper and evaporated to dryness under reduced pressure. An orangey oil (14.8 g) of 2-methylthio-1,3-dinitrobenzene is obtained. This oil is dissolved in 30 ml of 96° ethanol and added dropwise to a suspension, heated to reflux, of 2.9 g of ammonium chloride and 63 g of finely-powdered zinc in 180 ml of alcohol and 26 ml of water.

The reaction is exothermic.

The colorless reaction medium is filtered while boiling. The filtrate is cooled to 0° C. and acidified with 24 ml of an approximately 7N solution of hydrochloric acid in absolute ethanol.

After diluting with 1.5 ml of acetone, the expected dihydrochloride crystallizes.

The white crystals are filtered off, washed with acetone and dried under vacuum, over potassium hydroxide, at 40° C.

There are obtained 7.3 g of the expected dihydrochloride, melting with decomposition at 240°–245° C. and of which the elemental analysis, calculated for $C_7H_{12}N_2SCl_2$, is

| % | C | H | N | S | Cl |
|---|---|---|---|---|---|
| Calculated | 37.01 | 5.32 | 12.33 | 14.12 | 31.21 |
| Found | 37.06 | 5.32 | 12.35 | 14.10 | 31.33 |

Example 2

Preparation of 2-(β-acetylaminoethylthio)-1,3-diaminobenzene dihydrochloride

1st stage: Synthesis of 2-(β-acetylaminoethylthio)-1,3-dinitrobenzene.

10 g of potassium hydroxide powder are dissolved in a solution of 35.7 g (0.3 mol) of N-(2-mercaptoethyl) acetamide in 100 ml of dimethoxyethane heated to 45° C.

After cooling to 15° C., a solution of 24.3 g (0.12 mol) of 2-chloro-1,3-dinitrobenzene in 50 ml of dimethoxyethane is run in dropwise over 30 min.

The temperature is maintained between 15° and 20° C. for an additional 30 min.

The reaction mixture is poured into 300 ml of ice-cold water.

The orangey-yellow crystalline precipitate is filtered off, reslurried in water and dried under vacuum at 30° C. over phosphorus pentoxide.

After recrystallizing from 96° ethanol, there are obtained 15.7 g of yellow crystals melting at 110° C. and of which the elemental analysis, calculated for $C_{10}H_{11}N_3O_5S$, is

| % | C | H | N | O | S |
|---|---|---|---|---|---|
| Calculated | 42.10 | 3.89 | 14.73 | 28.04 | 11.24 |
| Found | 42.32 | 3.93 | 14.68 | 27.84 | 11.18 |

2nd stage: Reduction

The reduction of the compound obtained above in the 1st stage is carried out according to the procedure described for Example 1.

The dihydrochloride obtained is purified by recrystallization from a water/ethanol (1/6) mixture at reflux.

There are obtained white crystals melting with decomposition at 197°–200° C. and of which the elemental analysis, calculated for $C_{10}H_{17}N_3OSCl_2$, is:

| % | C | H | N | O | S | Cl |
|---|---|---|---|---|---|---|
| Calculated | 40.27 | 5.75 | 14.09 | 5.36 | 10.75 | 23.78 |
| Found | 40.08 | 5.80 | 14.06 | 5.85 | 10.68 | 23.60 |

Example 3

Preparation of 2-methylthio-5-methyl-1,3-diaminobenzene dihydrochloride

1st stage: Synthesis of 2-methylthio-5-methyl-1,3-dinitrobenzene

A solution of 50.0 g (0.231 mol) of 2-chloro-5-methyl-1,3-dinitrobenzene in 140 ml of dimethoxyethane is added dropwise, over one hour and while maintaining the temperature between 17° C. and 20° C., to a suspension of 25 g (0.35 mol) of sodium thiomethylate in 250 ml of dimethoxyethane.

After stirring for one hour at room temperature, the reaction mixture is run into 1.5 l of ice-cold water.

The crystalline precipitate is filtered off, reslurried in water, dried and then recrystallized from boiling ethyl acetate.

There are obtained 22.2 g of pale-yellow crystals melting at 106° C. and of which the elemental analysis, calculated for $C_8H_8N_2O_4S$, is:

| % | C | H | N | O | S |
|---|---|---|---|---|---|
| Calculated | 42.10 | 3.53 | 12.27 | 28.04 | 14.05 |
| Found | 42.18 | 3.59 | 12.18 | 28.25 | 14.11 |

2nd stage: Reduction

A suspension, heated to reflux, of 4.4 g of ammonium chloride and 82 g of finely-powdered zinc in 280 ml of alcohol and 33 ml of water is treated portion-wise, so as to maintain the reflux without heating, with 20.5 g (0.09 mol) of the above dinitro compound obtained in the first stage.

The reaction is exothermic.

The reaction mixture is filtered while boiling, partially evaporated so as to remove the alcohol and extracted with ethyl ether.

After drying over sodium sulfate and filtering, the ether phase is acidified with 30 ml of an approximately 6N solution of hydrochloric acid in absolute ethanol.

The 2-methylthio-5-methyl-1,3-diaminobenzene dihydrochloride precipitate is filtered off and dried over potassium hydroxide.

There are obtained 15.2 g of white crystals recrystallized from an ethanol/water mixture melting with decomposition at 220°–224° C. and of which the elemental analysis, calculated for $C_8H_{12}N_2S.2HCl$, is:

| % | C | H | N | S | Cl |
|---|---|---|---|---|---|
| Calculated | 39.84 | 5.85 | 11.61 | 13.29 | 29.40 |
| Found | 39.65 | 5.89 | 11.81 | 13.20 | 29.30 |

Example 4

Preparation of 2-methylthio-5-amido-1,3-diaminobenzene dihydrochloride

1st stage: Synthesis of 2-methylthio-5-amido-1,3-dinitrobenzene

This compound is prepared according to the procedure described for Example 3, Stage 1.

There are obtained, from 24.6 g (0.10 mol) of 2-chloro-5-amido-1,3-dinitrobenzene, 5.8 g of yellow crystals recrystallized from 96° ethanol, melting at 196° C. and of which the elemental analysis, calculated for $C_8H_7N_3O_5S$, is:

| % | C | H | N | O | S |
|---|---|---|---|---|---|
| Calculated | 37.36 | 2.74 | 16.34 | 31.10 | 12.47 |
| Found | 37.55 | 2.76 | 16.55 | 31.27 | 12.56 |

2nd stage: Reduction

The reduction is carried out according to the procedure described for Example 3, Stage 2.

There are obtained, from 12.5 g (0.0486 mol) of the dinitro compound obtained in the first stage, 3.6 g of white crystals, recrystallized from a water/ethanol mixture, of 2-methylthio-5-amido-1,3-diaminobenzene dihydrochloride, melting with decomposition at 230°–232° C. and of which the elemental analysis, calculated for $C_8H_{11}N_3OS.2HCl$, is:

| % | C | H | N | O | S | Cl |
|---|---|---|---|---|---|---|
| Calculated | 35.56 | 4.85 | 15.55 | 5.92 | 11.87 | 26.24 |
| Found | 35.80 | 4.82 | 15.43 | 6.19 | 12.07 | 26.36 |

Example 5

Preparation of 2-methylthio-5-nitrilo-1,3-diaminobenzene monohydrochloride

1st stage: Synthesis of 2-methylthio-5-nitrilo-1,3-diaminobenzene

This compound is prepared according to the procedure described for Example 3, Stage 1.

There are obtained, from 7.5 g (0.033 mol) of 2-chloro-5-nitrile-1,3-dinitrobenzene, 3.7 g of yellow crystals, recrystallized from isopropyl acetate at reflux, melting at 137° C. and of which the elemental analysis, calculated for $C_8H_5N_3O_4S$, is:

| % | C | H | N | O | S |
|---|---|---|---|---|---|
| Calculated | 40.17 | 2.11 | 17.57 | 26.75 | 13.40 |
| Found | 40.29 | 2.17 | 17.59 | 26.93 | 13.45 |

2nd stage: Reduction

The reduction is carried out according to the process described for Example 3, Stage 2.

There are obtained, from 3.5 g (0.0146 mol) of the dinitro compound obtained in the first stage, after recrystallization from an ethanol/water mixture, 1.3 g of white crystals of 2-methylthio-5-nitrilo-1,3-diaminobenzene monohydrochloride melting with decomposition at 198°–200° C. and of which the elemental analysis, calculated for $C_8H_9N_3S.HCl$, is:

| % | C | H | N | S | Cl |
|---|---|---|---|---|---|
| Calculated | 44.55 | 4.67 | 19.48 | 14.86 | 16.44 |
| Found | 44.66 | 4.76 | 19.64 | 15.00 | 16.43 |

Dyeing at acid pH
Composition A

| | |
|---|---|
| Oleyl alcohol polyglycerolated with 2 mol of glycerol | 4.0 g |
| Oleyl alcohol polyglycerolated with 4 mol of glycerol at 78% AM | 5.69 g AM |
| Oleic acid | 3.0 g |
| Oleyl amine containing two mol of ethylene oxide sold under the name Ethomeen O12 by the company Akzo | 7.0 g |
| Diethylaminopropyl laurylamino succinamate, sodium salt at 55% AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Monomethyl ether of propylene glycol | 9.0 g |
| Sodium metabisulfite as a 35% aqueous solution | 0.455 g |
| Ammonium acetate | 0.8 g |
| Antioxidizing agent, sequestering agent | q.s. |
| Fragrance, preserving agents | q.s. |
| Monoethanolamine | q.s. for pH 9.8 |
| Dyes | x g |
| Demineralized water | q.s. for 100.0 g |

Composition B

It consists of a 20 volumes hydrogen peroxide solution, the pH of which is adjusted between 1 and 1.5 with orthophosphoric acid.

Dyeing protocol

Composition A is mixed, weight for weight, with Composition B containing hydrogen peroxide. The mixture obtained is applied to permanent wave or non-permanent wave natural gray hair containing 90% white hairs for 30 minutes. The hair is then rinsed, washed with shampoo, then rinsed again and dried.

| EXAMPLES | 1 | 2 | 3 | 4 | 5 |
|---|---|---|---|---|---|
| Composition A containing: | | | | | |
| 2-(β-acetylaminoethylthio)-1,3-diaminobenzene dihydrochloride | 0.89 g | | | | |
| 2-methylthio-1,3-diaminobenzene dihydrochloride | | 0.68 g | | | |
| 2-methylthio-5-methyl-1,3-diaminobenzene dihydrochloride | | | 0.724 g | | |
| 2-methylthio-5-nitrilo-1,3-diaminobenzene [sic] monohydrochloride | | | | 0.080 g | |
| 2-methylthio-5-trifluoromethyl-1,3-diaminobenzene monahydrochloride | | | | | 0.050 g |
| 2,6-dimethylparephenylenediamine paraphenylenediamine | 0.41 g | 0.41 g | | | |
| 2,4-diaminophenoxyethanol dihydrochloride | | | 0.324 g | 0.324 g 0.651 g | 0.675 g |
| 2,6-dimethylparaphenylenediamine dihydrochloride | | | | | 0.627 g |
| Mixture, weight for weight, of A and B | | | | | |
| pH of the mixture | 6.4 | 6.3 | 6.4 | 6.5 | 6.3 |
| Shades obtained | | | | | |
| •on natural grey hair containing 90% white hairs | blue slightly green | | golden mahogany | | medium blue |
| •on permanent wave natural gray hair containing 90% white hairs | | midnight blue | | deep blue-black | |

Dyeing at basic pH

Composition C

| | |
|---|---|
| Octyldodecanol sold under the name Eutanol D by the company Henkel | 8.0 g |
| Oleic acid | 20.0 g |
| Monoethanolamine laurylethersulfate sold under the name Sipon LM 35 by the Company Henkel | 3.0 g |
| Ethyl alcohol | 10.0 g |
| Benzyl alcohol | 10.0 g |
| Cetylstearyl alcohol containing 33 mol of ethylene oxide sold under the name Simulsol GS by the Company Seppic | 2.4 g |
| Ethylenediaminetetraacetic acid | 0.2 g |
| Aqueous solution containing 60% AM of a cationic polymer having the following repeating unit: | 3.7 g |

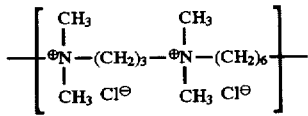

| | |
|---|---|
| Monoethanolamine | 7.5 g |
| Diethanolamide of linoelic acid sold under the name Comperlan F by the Company Henkel | 8.0 g |
| Aqueous ammonia containing 20% NH₃ | 10.2 g |
| Sodium metabisulfite as a 35% aqueous solution | 1.3 g |
| Hydroquinone | 0.15 g |
| Dyes | x g |
| Demineralized water q.s. for | 100.0 g |

Composition D 20 volumes hydrogen peroxide at pH=3.

Dyeing protocol

Composition C is mixed, weight for weight, with Composition D. The mixture obtained is applied to permanent wave or non-permanent wave natural gray hair containinig 90% white hairs for 30 min. The hair is then rinsed, washed with shampoo, then rinsed again and dried.

| EXAMPLES | 6 | 7 | 8 | 9 | 10 | 11 | 12 | 13 |
|---|---|---|---|---|---|---|---|---|
| Composition C containing: | | | | | | | | |
| 2-(β-acetylaminoethyl-thio)-1,3-diaminobenzene dihydrochloride | 0.60 g | | 1.20 g | | | | | |
| 2-methylthio-1,3-diaminobenzene dihydrochloride | | 0.45 g | | 0.90 g | | | | |
| 1-phenyl-3-methyl-5 pyrazolene | | | | | | 0.2 g | 0.2 g | 0.2 g | 0.2 g |
| 2-methylthio-5-methyl-1,3-diaminobenzene di- | | | | | 0.965 g | | | |

| EXAMPLES | 6 | 7 | 8 | 9 | 10 | 11 | 12 | 13 |
|---|---|---|---|---|---|---|---|---|
| hydrochloride | | | | | | | | |
| 2-methylthio-5-amido-1,3-diaminobenzene dihydrochloride | | | | | | 0.337 g | | |
| 2-methylthio-5-trifluoromethyl-1,3 diaminobenzene monohydrochloride | | | | | | | 0.468 g | |
| 2-methylthio-5-nitrilo-3-diaminobenzene monohydrochloride | | | | | | | | 0.100 g |
| paraphenylenediamine | 0.22 g | 0.22 g | | | | 0.216 g | | 0.216 g |
| 2-methoxymethyl-4-aminophenol | | | 0.61 g | 0.61 g | | | | |
| paraminophenol | | | | | 0.436 g | | 0.327 g | |
| 2,4-diaminophenoxy-ethenol dihydrochloride | | | | | | 0.170 g | | |
| 2-methyl-5-N-(β-hydroxyethyl)-aminophenol | | | | | | | 0.05 g | 0.251 g |
| Mixture, weight for weight, of C and D | 10.4 | 10.2 | 10.3 | 10.4 | 10.4 | 10.5 | 10.3 | 10.5 |
| pH of the mixture | | | | | | | | |
| Shades obtained: | | | | | | | | |
| •on natural gray hair containing 90% % white hairs | blue-green | | green | | golden coppery | | | purplish beige |
| •on permanent wave natural gray hair containing 90% white hairs | | strong blue | | bluish green | | blue | slightly iridescent coppery | |

We claim:

1. A 2-sulfurated metaphenylenediamine having the formula

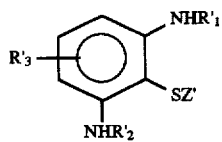

wherein

Z' represents $C_1-C_{18}$ alkyl, aralkyl wherein the alkyl moiety is $C_1-C_6$, $C_1-C_6$ monohydroxyalkyl, $C_2-C_6$ polyhydroxyalkyl, aryl, aminoalkyl having the formula

wherein n is an integer from 1 to 6;

$R'_4$ and $R'_5$, each independently, represent hydrogen, $C_1-C_4$ alkyl, $C_1-C_4$ hydroxyalkyl or $C_1-C_6$ acyl;

$R'_1$ and $R'_2$, each independently, represent hydrogen, $C_1-C_6$ alkyl, $C_1-C_6$ monohydroxyalkyl, $C_2-C_6$ polyhydroxyalkyl, $C_1-C_6$ monocarbamoylalkyl, $C_1-C_6$ dialkylcarbamoyl, $C_1-C_6$ aminoalkyl, $C_1-C_6$ acyl, $C_2-C_6$ carbalkoxy, carbamyl or $C_1-C_6$ monoalkylcarbamoyl;

$R'_3$ represents hydrogen, $C_1-C_4$ alkyl, nitrile, amide, $C_1-C_4$ fluoroalkyl or —COOR wherein R represents hydrogen or $C_1-C_4$ alkyl; and the acid salt thereof, with the proviso that:

(a) when $R'_1$, $R'_2$ and $R'_3$ represent hydrogen, Z' is other than said $C_1-C_{18}$ alkyl or said aryl;

(b) when Z' represents methyl and $R'_3$ represents hydrogen, $R'_1$ and $R'_2$ do not represent the same $C_1-C_6$ acyl, (c) when Z' represents methyl and when $R'_3$ represents hydrogen and when one of $R'_1$ and $R'_2$ represents hydrogen, the other $R'_1$ and $R'_2$ do not represent a $C_4$ acyl;

(d) when $R'_1$ and $R'_2$ represent hydrogen and $R'_3$ represents a trifluoromethyl in the 5 position, Z' does not represent $C_1-C_4$ alkyl; and (e) when $R'_1$ and $R'_2$ represent hydrogen and $R'_3$ represents methyl in the 4 position, Z' does not represent methyl.

2. A 2-sulfurated metaphenylenediamine selected from the group consisting of 2-(β-acetylaminoethylthio)-1,3-diaminobenzene, 2-methylthio-5-methyl-1,3-diaminobenzene, 2-methylthio-5-amido-1,3-diaminobenzene and 2-methylthio-5-nitrilo-1,3-diaminobenzene.

* * * * *